United States Patent
Wood et al.

[11] Patent Number: 6,083,264
[45] Date of Patent: Jul. 4, 2000

[54] IMPLANT MATERIAL FOR REPLACING OR AUGMENTING LIVING BONE TISSUE INVOLVING THERMOPLASTIC SYNTACTIC FOAM

[75] Inventors: David W. Wood; James L. Melquist; Walter A. Phillips, all of Tempe; Donald J. Bridges, Mesa, all of Ariz.

[73] Assignee: McDonnell Douglas Corporation, St. Louis, Mo.

[21] Appl. No.: 09/107,364

[22] Filed: Jun. 30, 1998

[51] Int. Cl.[7] .................................................. A61F 2/28
[52] U.S. Cl. ............................ 623/23.056; 623/16.11; 501/1; 523/116
[58] Field of Search ......................... 623/11, 16; 501/1, 501/12; 523/113, 116

[56] References Cited

U.S. PATENT DOCUMENTS

| | | | |
|---|---|---|---|
| 3,936,887 | 2/1976 | Hodosh | 623/10 |
| 3,986,213 | 10/1976 | Lynch | 623/8 |
| 4,222,128 | 9/1980 | Tomonaga et al. | 623/16 |
| 4,863,974 | 9/1989 | Mallouk et al. | 521/85 |
| 5,071,436 | 12/1991 | Huc et al. | 623/16 |
| 5,092,890 | 3/1992 | Pohlemann et al. | 623/16 |
| 5,152,791 | 10/1992 | Hakamatsuka et al. | 623/16 |
| 5,192,325 | 3/1993 | Kijima et al. | 623/16 |
| 5,340,352 | 8/1994 | Nakanishi et al. | 623/7 |
| 5,356,436 | 10/1994 | Nonami et al. | 623/16 |
| 5,366,508 | 11/1994 | Brekke | 623/16 |
| 5,522,895 | 6/1996 | Mikos | 623/16 |
| 5,532,295 | 7/1996 | Harrison et al. | 523/218 |
| 5,645,591 | 7/1997 | Kuberasampath et al. | 623/16 |
| 5,650,108 | 7/1997 | Nies et al. | 264/122 |
| 5,676,699 | 10/1997 | Gogolewski et al. | 623/16 |
| 5,683,459 | 11/1997 | Brekke | 623/16 |
| 5,683,461 | 11/1997 | Lee et al. | 623/16 |
| 5,684,061 | 11/1997 | Ohnishi et al. | 523/114 |
| 5,686,091 | 11/1997 | Leong et al. | 424/426 |
| 5,691,390 | 11/1997 | Harrison et al. | 521/54 |

FOREIGN PATENT DOCUMENTS

| | | |
|---|---|---|
| 560418 | 9/1993 | European Pat. Off. . |
| 952842 | 3/1964 | United Kingdom . |
| 1548419 | 7/1979 | United Kingdom . |

*Primary Examiner*—Paul B. Prebilic
*Attorney, Agent, or Firm*—Westerlund & Powell, P.C.; Robert A. Westerlund; Ramon R. Hoch

[57] ABSTRACT

An implant device material is provided for replacement or augmentation of living bone tissue involving a thermoplastic syntactic foam material formed from microballoons, a polymer such as polyetherimide which wets and binds the microballons into an array, and interstitial space is present between the microballoons bound into the array to create porosity. A fiber material can be embedded within the array. The thermoplastic syntactic foam material is highly biocompatible and stable with no apparent adverse effects on a recipient. The implant device material also effectively conducts bone into the porous implant via its controlled interstitial porosity. The implant material also can be readily molded or machined into complex structural shapes, density and porosity, such that it can be closely tailored to mimic the natural bone tissue to be replaced.

17 Claims, 3 Drawing Sheets

IMPLANT MATERIAL FOR REPLACING OR AUGMENTING LIVING BONE TISSUE INVOLVING THERMOPLASTIC SYNTACTIC FOAM

BACKGROUND OF THE INVENTION

The present invention relates to synthetic bone implants and methods for installing same in a living body, and more particularly to synthetic implants which induce osteogenesis in vivo.

Trauma, surgical or orthopaedic procedures, congenital deformities, or degenerative conditions, can result in the loss or absence of natural bone tissue which often requires prosthetic operations in order to replace the missing bone tissue.

Bone is a natural composite material composed of a matrix of organic (viz. collagen) and inorganic (viz., apatite) constituents. In the United States alone, is estimated that well over 1,000,000 patients annually require bone augmentation, and, of these, less than half receive human donor materials. As to the latter source of implant bone material, allograft materials are limited in use, tend to have unpredictable, non-reproducible mechanical properties, and have potential for disease transmission. On the other hand, the removal of autologous bone from the epihyses and metaphyses involving the thigh bone and the tibia, or the iliac crest or rib of a patient for grafting purposes requires that the patient endure an additional surgical procedure and the size and shaping of bone grafts taken in this manner may be inadequate for the correction needed.

As artificial bone implant materials, metals and ceramics have been used to replace missing or diseased portions of bone. However, these materials have several disadvantages when implanted in the human body. Ceramic materials tend to embrittle and release powder generated by abrasion into the surrounding biological tissues. Additionally, composites of ceramic or metals with polymers have been proposed for bone implants but the strengths and/or resistance to embrittlement are not completely satisfactory. Non-porous, solid phase implant materials based on mixtures of polymer and apatite used for replacing hard tissue have been described, for example, in U.S. Pat. No. 5,092,890.

As to metal implants, the elastic modulus of metallic implants (e.g., titanium and chrome) generally are 8 to 16 times greater than that of bone resulting in stress shielding across the implant-cement-bone. This leaves the bone virtually inactive and unstressed resulting in re-sorption, thus enlarging the cavity, and susceptible to infectious reactions. Also, metals ions can elute from a metal implant to cause adverse effects upon surrounding biological tissues. Additionally, by comparison, natural bone is porous, thereby allowing for bone ingrowth, soft tissue compatibility, internal capillary growth, fluid flow, and so forth, which are attributes not possible with metals.

As can be appreciated from the above, an artificial bone replacement material has been in demand that has mechanical properties and ingrowth inducing properties that mimic natural bone. However, conventional bone implants that appeared to promote certain bone ingrowth merely become infiltrated with bone from direct conduction of natural bone present at the interface of the natural bone and bone implant.

Porous synthetic bone matrices have been proposed which are designed to be biodegradable, bioresorbable or reactive, such as described, for example, in U.S. Pat. Nos. 5,645,591, 5,522,895, 5,366,508, 5,676,699, 5,686,091, 5,071,436, 5,683,461 and 5,683,459. Temporary implant materials are not suitable for all cases where bone replacement is needed in traumatized bone tissue. More permanent bone implants having some porosity are described, for example, in U.S. Pat. Nos. 5,152,791, 5,356,436 and 5,192,325, which relate to porous ceramic-based implant materials or coatings therefor, while U.S. Pat. Nos. 5,684,061, 5,650,108, and 4,863,974 relate to bone replacement materials involving porous polymeric matrices. Of these, in U.S. Pat. No. 5,684,061, bone induction was reported for the described implant material, preferably a porous membrane formed of a copolymer of vinylidene fluoride and trifluoroethylene, for relatively small pore sizes, e.g., 0.6 and 5 $\mu$m but not for a larger pore size of 30 $\mu$m. Relatively large pore sizes generally can be expected to be needed to promote viable capillary and tissue ingrowth to sustain biological growth in many bone implant implementations. U.S. Pat. No. 5,650,108 describes a porous bone replacement and bone cement material formed of a solid polymer of acrylic or methacrylic acid, a liquid component of an acrylic monomer and coarse biocompatible particle granules of plastics or inorganic solids. The density and porosity of the bone cement are controlled by the choice of geometry of the solid granule additive. U.S. Pat. No. 4,863,974 describes bone growth material with a void volume of greater than 70% for filling defects in bone made of expanded polytetrafluoroethylene and calcium phosphate. Very high void volumes in a bone implant material could restrict the structural, mechanical capabilities of the implant material.

New, accurate, long-lasting, and efficacious forms of porous synthetic bone are needed that have the ability to assume the mechanical properties and histological characteristics of natural bone tissue including promotion of bone ingrowth.

SUMMARY OF THE INVENTION

The above and other objects and benefits are achieved by the present invention in which a method and implant device therefor is provided for replacement or augmentation of living bone tissue involving a thermoplastic syntactic foam ("TPSF") material comprised of providing an implant comprising a microballoon first component, a polymer second component which is wetted to the microballoons and binds the microballoons together in an array, and an air third component incorporated into the TPSF implant material forming voids in interstices between the microballoons.

In practicing a method of the invention, a site in a living body in need of bone tissue replacement or augmentation is identified and the aforesaid inventive TPSF implant material is inserted into the living body at the site in need of the bone tissue replacement or augmentation.

The TPSF implant material of this invention has high processing flexibility and it can be readily molded or machined into complex structural shapes with predesigned physical properties, such as strength, density and porosity, closely tailored to mimic the natural bone tissue to be replaced.

Additionally, the TPSF implant material of this invention is highly biocompatible in soft and hard living tissue. Further, vascular elements form within the TPSF implant material of this invention. The ability of the inventive implant material to conduct bone within its inner structure (matrix) at sites distant from the implant-to-natural bone interface so as to form a living composite is remarkable, and, coupled with its biocompatible properties, makes the TPSF implant material useful for a broad spectrum of medical applications involving the reconstruction of the skeleton and to the fabrication of orthopaedic and other bone contacting implants. For instance, the TPSF implant material can be used for treating mammalian bone deficits, voids, defects and other abscises produced by traumatic injury, surgery, congenital deformities, and atrophy, and the like. Specific applications include bone defect healing, as a prosthesis for oral-maxillo facial reconstruction, cerebral surgery, or as a structural skeletal member such as an invertebral spacer in the cervical, thorasic, or lumbar vertebra.

As shown by in vivo animal tests summarized in the examples set forth herein, the TPSF implant material of this invention has no adverse biological side effects due to its stable, inert nature, and it permits normal bone to grow into the matrix via its designed porosity.

BRIEF DESCRIPTION OF THE DRAWINGS

These and various other features and aspects of the present invention will be readily understood with reference to the following detailed description read in conjunction with the accompanying drawings, in which.

DETAILED DESCRIPTION OF THE INVENTION

The material used to form the implant of this invention originates as a dry mix and is molded into the form of the desired three-dimensional bone shape, or other hard tissue (e.g., cartilage) shape. For complex bone shapes, tools are generally required. The primary constituents of the TPSF implant material used for bone replacement and/or augmentation are a polymerizable plastic powder, microballoons, and air spaces incorporated within the implant material as voids.

Figure 1:
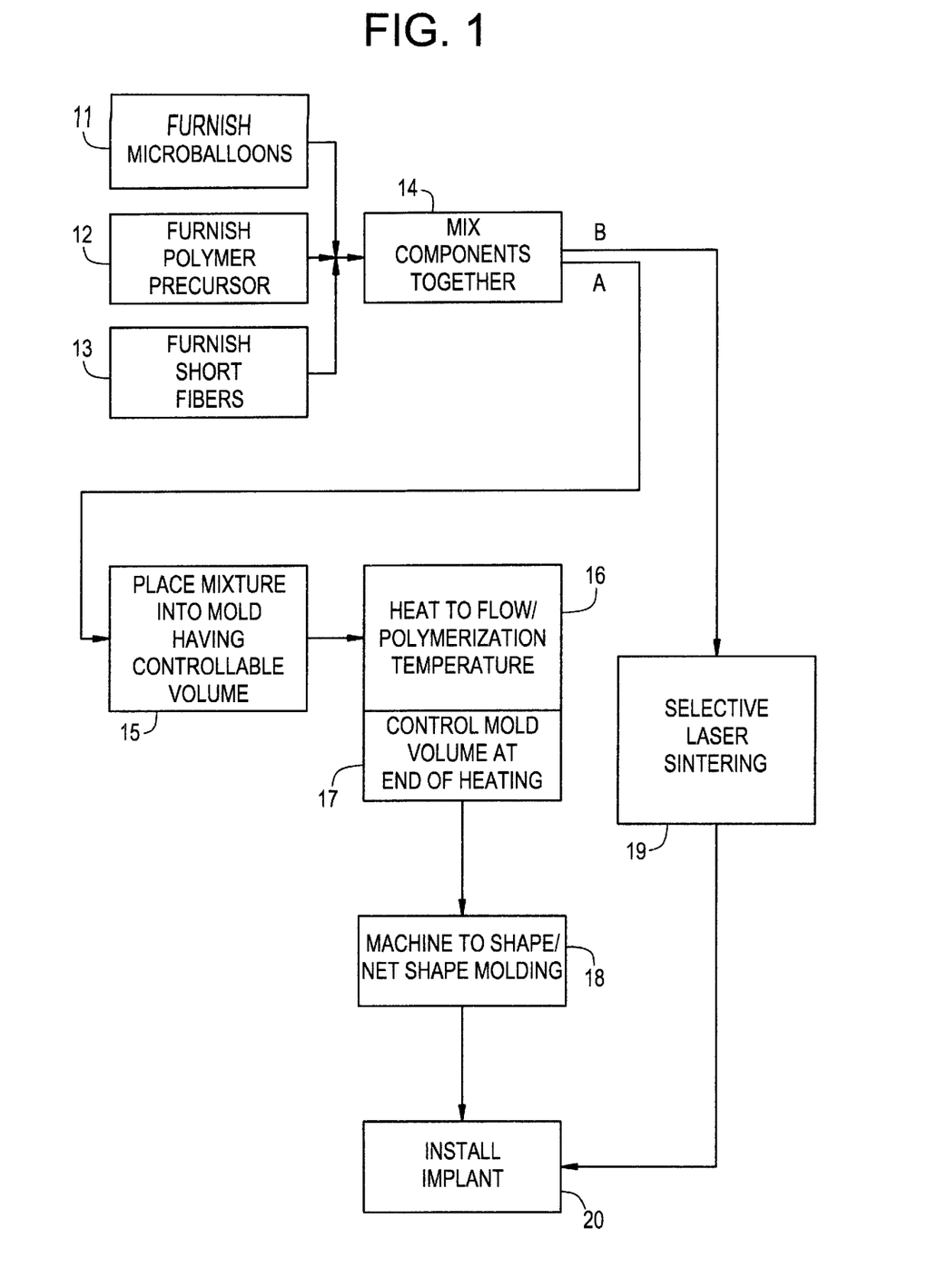
FIG. 1 is a process flow chart for the preparation and installation of an implant of the invention.

Referring now to FIG. 1, step 11 involves furnishing microballoons that are commercially available small, generally spherical, hollow bodies available in a range of diameters of several hundred micrometers or less, with wall thicknesses of about 1.5 micrometers. Preferably, the particle size of the microballoons lies within a range of 5 to 150 microns. The microballoon filler, also referred to as hollow microspheres or microbubbles, serve to adjust the foam density, strength, and stiffness. The shells or walls of the microballoons can be formed of glass, e.g., silica or borosilicates; ceramic, e.g., fly ash; or even polymers, such as phenolics. The preferred microballoons are spherical high-silica microballoons finished with N-phenylaminopropyl-trimethoxysilane surface coupling agent that are uniformly distributed throughout the matrix material. Surface-treated silica microballoons of this type are available under the trademark Eccospheres SI microballoons from Emerson & Cuming. Glass microballoons are also commercially available from Minnesota Mining & Manufacturing Co., St. Paul, Minn.

In step 12, a lower molecular weight, partially polymerized oligomeric precursor to a polyetherimide polymer is furnished. The prepolymer, terminated with reactive end groups, preferably has a structure as shown in formula I below:

Variants of the structure of formula I with diamino end cap and dianhydride end cap species are also operable. This oligomeric precursor is sold under the trademark ULTEM™ 1010P, and is available from General Electric Co. The polyetherimide polymer resulting from the polymerization of the prepolymer shown in formula I is known as ULTEM™ 1000, also a trademark of General Electric. This component is preferable due to its low initial viscosity in a preferred processing temperature of about 320–340° C. The prepolymer is a solid at ambient temperature and has a glass temperature of about 210° C. It is ground to particulate form, preferably between −140 to −400 mesh size for subsequent mixing. The relatively low initial viscosity permits the molten prepolymer to flow over the microballoons upon heating to a processing temperature well above the glass transition temperature. After flowing and covering the microballoons, the prepolymer polymerizes to a polyetherimide polymer.

In step 13, short fibers may optionally be used. The fibers can be used to reduce the bulk density of the mixed material and/or to tailor the electrical properties of the foam. For instance, chopped carbon fibers can be added to the mixture to create an artificial dielectric material. The dielectric constant of the foam can be adjusted by altering the fiber length and/or diameter; the loss tangent can be adjusted by selection of fiber resistivity; and the resonant frequency can be adjusted by fiber volume. In general, the fiber have diameter of no more than about 11 micrometers, a length of no more than 3000 micrometers, and the dielectric constant is controlled to be in the range of about 1.25 to 20. Besides fibers, the implant materials according to the invention can also contain other types of fillers that are biologically compatible and non-toxic, such as calcium compounds like apatite, i.e., $Ca_{10}(PO_4)(OH, F,Cl)_2$, hydroxyapatite, i.e., $Ca_{10}(PO_4)(OH)_2$, CaO, or calcium carbonate.

As indicated by step 14 in FIG. 1, the microballoons, solid oligomeric precursor powder, and any fibers or other fillers (when used) are mixed together. A carrier fluid such as water or an organic liquid (that is not a solvent for the polymer precursor or polymer), such as hexane, serves as a vehicle for the obtaining of a uniform distribution of microballoons, precursor particles, and any fibers. The solid components are dispersed in the carrier fluid, such as hexane, and the ingredients are stirred or agitated therein until the mixture appears uniform, and the thereafter the carrier fluid is removed (volatized) so that the uniform mixture is ready for further processing. Upon mixing, the mixture typically has a consistency akin to wet sand.

Figure 2:
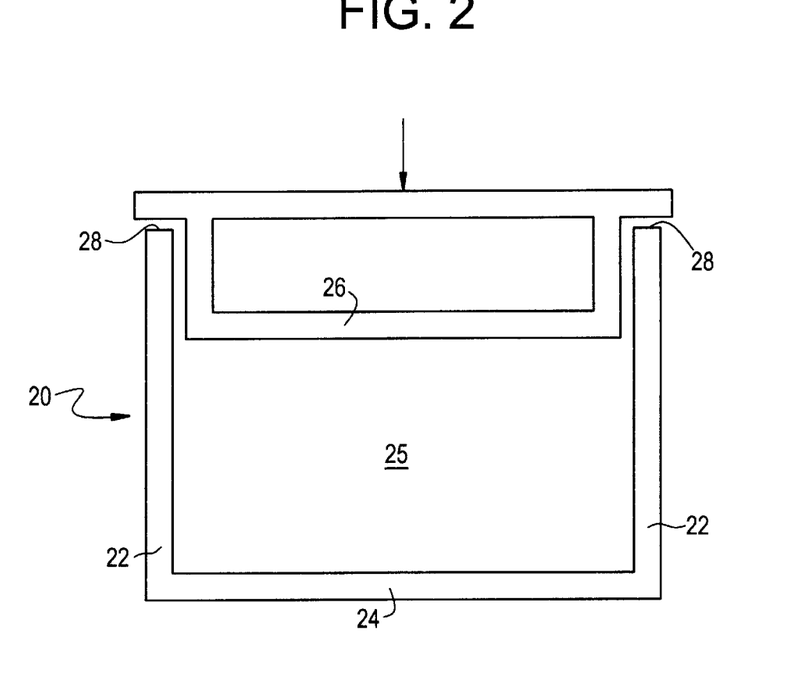
FIG. 2 is a cross-sectional schematic view of a mold used to prepare the implant.

In step 15, the mixture is introduced into a cavity 25 of a mold 20 having a controllable final volume. An example of such a mold 20 is shown in FIG. 2. The mold 20 has fixed side walls 22 and a fixed bottom 24. A top 26 is movable and is can slide downwardly between the side walls 22. Stops 28 on side walls 22 halt the downward movement of the top 26. A sufficient amount of the mixture of components is provided to initially fill the mold 20 to a level therein below stops 28 but above the location in mold 20 where top 26 will make its greatest downward movement into mold 20.

Returning to FIG. 1, in step 16 thereof, the mold and contained mixture are heated to the processing temperature, preferably from about 320 to about 350° C., by placing them into a furnace operating at that temperature. As the oligomeric precursor is heated above its glass transition temperature of about 210° C., it softens and flows around the microballoons to wet and encapsulate them. The wetting of the microballoons is important to the final mechanical properties of the implant material. An absence of wetting leads to a weak product.

The mass can be compressed due to the flowing of the oligomeric precursor. The weight of the mold top 26 (and added force, if necessary) compresses the mass of oligomeric precursor, microballoons, and optional fibers. In step 17, simultaneously with the heating, the final interior volume of the mold is determined. The mold top 26 gradually moves downwardly until its movement is halted by the stops 28.

Because the microballoons are largely incompressible under the heating conditions, the downward movement of the top 26 compresses the oligomeric precursor, and fibers (if present), into any voids found within the structure. Air is displaced and driven out of the mass by the downward mold compression. The amount of air that is displaced is governed by the extent of compression and downward movement of the mold top 26. The more air that is displaced, the higher the density and the higher the strength of the final material. As a requirement of this invention, it is imperative that sufficient air spaces be preserved in the TPSF implant material so that the implant device, as installed in a living body, can promote and sustain osteogenesis. In general, in the final product, the amount of air is preferably from about 3 to about 70 parts by volume per 100 parts product, where this numerical range does not factor in the air inside the microballoons.

Continued heating at the processing temperature causes the oligomeric precursor to chain extend and imidize, forming a high molecular weight polyetherimide polymer. The total time required at the processing temperature to complete the reaction is from about 30 to about 90 minutes, preferably about 60 minutes.

As indicated as step 18 in FIG. 1, the molded piece is machined to remove any molding flash, and the like, and to refine the geometric form of the molded piece to correspond to the desired shape of the artificial bone TPSF implant material to be installed.

It will be understood that the ultimate desired geometric form of the artificial bone TPSF implant material of this invention can be achieved by several conventional shaping methods involving molding, machining, and/or laser sintering, and they are not merely limited to the approach illustrated above using steps 15–18 (i.e., process route "A"). Anatomical form and complex internal structures can be achieved using rapid prototyping technology. For instance, anatomical form can be acquired through tomographic methods (CT or MRI). For instance, the desired geometric form of the implant can be fabricated using selective laser sintering techniques, which is indicated as alternate process route "B" in FIG. 1, such as a selective laser sintering powder rolling system. The encapsulate melting temperature of the polyetherimide polymer precursor described hereinabove is consistent with local melting and fusion when swept by a carbon dioxide laser used in selective laser sintering. Thus, as an alternative approach to progressing through steps 15–18 in FIG. 1, a selective laser sintering powder rolling system and sintering method could instead be used pursuant to step 19 to heat and polymerize the implant material into a desired shape. Implant product forming with selective laser sintering can provide more flexibility, if needed, in structural design, support automated parts fabrication, provide density tailoring, allow formation of internal structures (e.g., trusses, ribs, spars, and so forth), and shorten development time. The inventive TPSF material is easy to handle and is adaptible to many different sizes and shapes.

Figure 3:
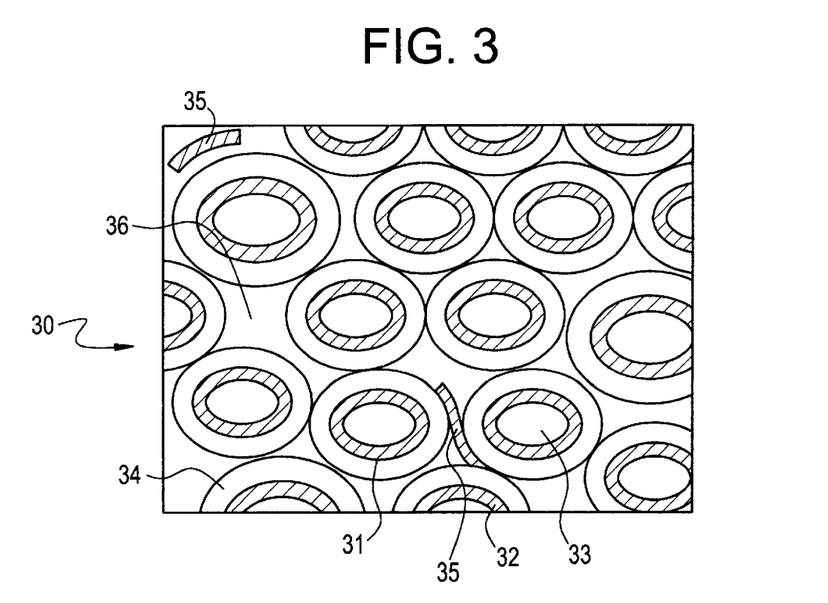
FIG. 3 is a cross-sectional schematic drawing of the microstructure of the implant of the invention.

FIG. 3 is a drawing representative of the microstructure of the TPSF implant material produced by the above-described processing. Microballoons 31 include a largely silica shell or wall 32 enclosing a void 33. The exterior of the wall 32 of the microballoons 31 is covered with a layer 34 of polyetherimide polymer that wets the microballoons. The adjacent layers 34 bond together, bonding the microballoons into an irregular array. Optionally present fibers 35 are shown within the array, and are also bonded into the array by the polyetherimide polymer. Within the array 30, there are air filled interstices or voids 36, which do not include the spaces completely enclosed by the microballoons 31 per se. The relative amount of the interstices 36 and parts of the air component constituted thereby are determined by the extent of compression of the mass while in the mold 20 during the fabrication procedure. The material 30 is a syntactic material by virtue of the presence of the hollow microballoons and controlled interstitial porosity. The air spaces 36 can be likened to air spaces in a popcorn ball type of structure. The polymeric material itself is not literally "foamed" within the customary meaning of that terminology. However, the implant material of this invention is occasionally referred to herein as a "thermoplastic syntactic foam" (TPSF) in light of its foam-like attributes. Interestingly, the microballoons tend to create a closed-cell foam-like structure while the interstitial porosity (air voids) tend to create an open-cell foam-like structure.

Returning again to FIG. 1, in the final step 20, the fabricated implant material is installed in a living body, e.g., a mammalian body, at site therein in need of bone replacement or augmentation. Prior to implantation and following explantation after sufficient time has been afforded for osteogenesis to occur, the implant materials of this invention are stronger in compression than human cancellous bone.

The mixing ratios of the primary ingredients, i.e., the microballoons, polymerizable plastic powder, and optional fibers used to fabricate the implant used in step 20 can be judiciously varied to bring about a correspondence in density, strength, stiffness, and/or porosity that closely matches and mimics the natural bone to be replaced. For instance, an implant for use in an oral-maxillo facial reconstruction application generally will not require as high an interstitial porosity as compared to a tibial replacement. By changing the microballoon size, polymer to balloon mixing ratio, and compressive pressure of formation to control the amount of air space voids, the density, degree of porosity, strength, stiffness and other physical properties of the implant product can be controlled as needed for the particular bone replacement of interest.

In general, the oligomeric precursor of the polyetherimide (i.e., the prepolymer) and the microballoons can be blended to provide a composite implant product density ranging anywhere from about 10 to about 70 lb/ft$^3$, with the composite density generally increasing with increased volume fraction of the prepolymer relative to the volume fraction of the microballoons component, and decreasing with decreased volume fraction of the prepolymer relative to the volume fraction of the microballoons component. For many bone replacement implementations, the volume fraction of the microballoons in the composite implant product generally ranges from about 3 to 85 parts by volume, more typically about 25 to 70 parts by volume, the volume fraction of the prepolymer in the composite implant product generally ranges from about 85 to 3 parts by volume, more typically about 15 to 30 parts by volume, and the amount of interstitial air space within the TPSF implant material (excluding air space enclosed within microballoons) constituting about 3 to 70 parts by volume.

Experimental studies to evaluate in vivo the use of the TPSF implant material as synthetic, artificial bone have been successfully performed by the present investigators. The results, summarized in the examples herein, showed viable bone growth into the porous implant with no apparent adverse effects to the recipient. The implant was stable, inert, did not cause adverse reactions, and it promoted and sustained osteogenesis. The demonstrated ability of the implant to conduct bone within its matrix is remarkable, and, coupled with its biocompatibility properties, indicates broad medical applications to the reconstruction of the skeleton and to the fabrication of orthopaedic and other implants.

The following non-limiting examples are illustrative of the invention.

EXAMPLES

Example 1

Twelve New Zealand White rabbits had two cylinders of TPSF implant material simultaneously implanted, one in each tibial defect, wherein the two cylinders had different formulations from each other as described herein. New Zealand White rabbits were selected as the subjects because the model has been previously shown to be analogous to man in its rate and histological characteristics during bone wound healing.

Due to the difference in formulations, the two test cylinders differed in mean pore size. At termination, mechanical strength, biocompatibility, and bone conduction into the implant were assessed.

Thermoplastic syntactic foam was formulated according to two different formulations: a first batch formulated with 50 $\mu$m (mean diam.) silica microballoons and a second batch formulated with 95 $\mu$m (mean diam.) silica microballoons. The microballoons were obtained as Eccospheres SI microballoons from Emerson & Cuming. The oligomeric precursor material used to make the polyetherimide was ULTEM™ 1010P made by General Electric Co. Specimens of the TPSF implant material were prepared according to the fabrication procedure discussed above and illustrated in FIG. 1. The two tested TPSF implant material formulations (after completion of molding) were determined to be as follows:

Implant Formulation 1:
53.7 vol. parts 50 $\mu$m microballoons
18.9 vol. parts polyetherimide
27.4 vol. parts air (interstitial voids, excluding air entrapped in microballoons)

Implant Formulation 2:
57.6 vol. parts 95 $\mu$m microballoons
20.3 vol. parts polyetherimide
22.1 vol. parts air (interstitial voids, excluding air is entrapped in microballoons)

Scanning Electron Micrograph (SEM) examination of the TPSF implant material formulated with the 50 $\mu$m (ave. diam.) microballoons at 100× magnification revealed the presence of pore sizes therein of greater than 50 $\mu$m.

Scanning Electron Micrograph (SEM) examination of the TPSF implant material formulated with the 95 $\mu$m (ave. diam.) microballoons at 100× magnification revealed the presence of pore sizes therein of greater than 100 $\mu$m.

Experimental protocol:

Each of twelve rabbits had two implants simultaneously placed, one bilaterally in each tibia defect, with one implant made of formulation 1 and the second implant made of formulation 2. A 5 mm drilled defect was made in the cortex of the medial tibial metaphysis. TPSF implant material was placed in the defect and primary skin closure was achieved. Following a 12-week period to allow for osseous integration, the animals were sacrificed for histological and mechanical testing. At necropsy, animals were randomly separated into histological and mechanical groups.

Mechanical testing methods:

Compressive testing of the explanted TPSF implant materials was performed to determine the strength of the TPSF implant material once implanted in bone. The two formulations tested were compared to determine the effect of pore size and implantation on strength. Unimplanted (naive) and explanted cylinders were tested in compression. Rectangles of naive materials were tested in four point bending. Analysis of variance (ANOVA), t-test and Tukey's means comparison methods were done in a routine manner to determine the effect of pore size and implantation.

Ten implanted cylindrical specimens, five from each of the two formulations 1 and 2, were received for mechanical testing. These specimens arrived still within the tibia of the subject New Zealand white rabbits. Each tibia was individually packaged in a peel pack and labeled with animal number and side. Specimens were stored frozen at 18° F.

Twelve unimplanted cylindrical specimens (six of each formulation) were used as naive control specimens. Twenty bending specimens (ten from each formulation) were also received for testing. These specimens were square in cross-section and approximately three inches long. The naive specimens required no special preparation prior to testing.

The tibia containing the cylindrical specimen to be tested was removed from the freezer and allowed to thaw for 15 minutes. Any remaining soft tissue was removed. The medial metaphyseal surface was identified and sandpaper used to both expose the specimen and give the specimen a flat surface. The tibia was sectioned 2 to 5 mm distal to the implant with a cut perpendicular to the long axis. Working within the medullarly space, soft tissue surrounding the implant was removed and any adhesions to the inside surface of the space severed. A 0.25 inch diameter trephine, without a centering drill, was used to cut through the cortical bone and free the specimen from the tibia. The end of the specimen which had been in the medullarly space was trimmed with a scalpel so that this end was parallel with the cortical end and perpendicular to the long axis.

Mechanical testing was conducted on a MTS Sintech 1/S material test frame with a 1000 lbf load cell and a 50 lbf load cell. Both load cells were daily calibrated in accordance with ASTM E4-96 during the tests using a shunt resistor method. Test control and data acquisition were performed with Testworks for Windows software, a product of MTS Systems Corp.

Figure 4:
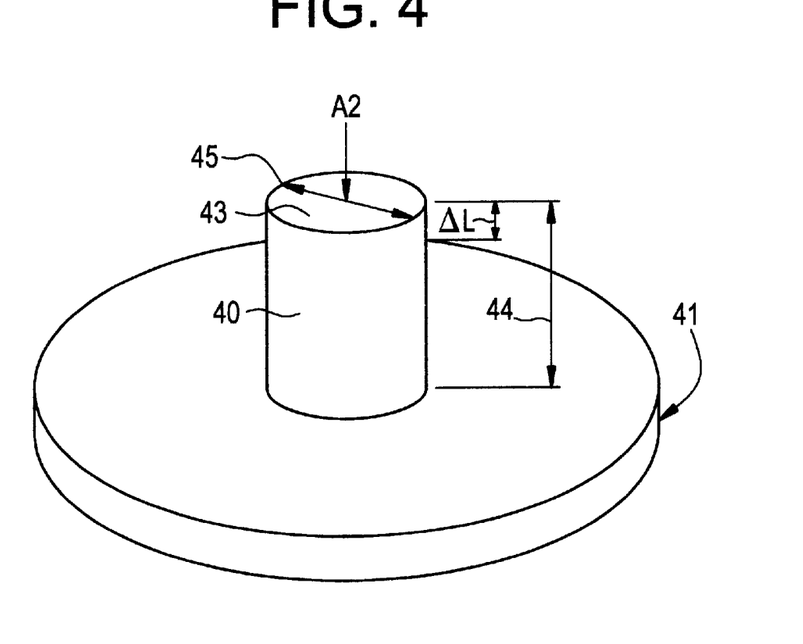
FIG. 4 is a schematical view of a specimen and platen arrangement used in compression tests performed on cylindrical specimens of explanted bone implants of this invention.

Compression testing was performed on the cylindrical specimens, and the length and diameter of each specimen was recorded, using the compression specimen and lower platen arrangement shown in FIG. 4. The specimen 40 to be tested was placed flat on a lower, fixed platen 41. A load 42 was applied evenly across the diameter 15 of the specimen 40 at displacement rate of 0.1 inches per minute to the upper specimen surface 43 until failure occurred (i.e., the specimen fractured). The 2% offset load, offset stress, and the modulus were recorded for each specimen 40.

Four definitions are relevant the compression results presented herein, which are as follows:

1) the 2% offset load of a specimen 40 was defined as the load value after the specimen 40 has been deformed 2% of the gage length 44;

2) stress was defined as the force applied per unit area of the upper face 43 of the specimen 40;

3) strain was defined as a measure of deformation (ΔL) per unit gage length 44 as a load was applied; and 4) modulus was the ratio of stress vs. strain in a specimen 40.

Figure 5:
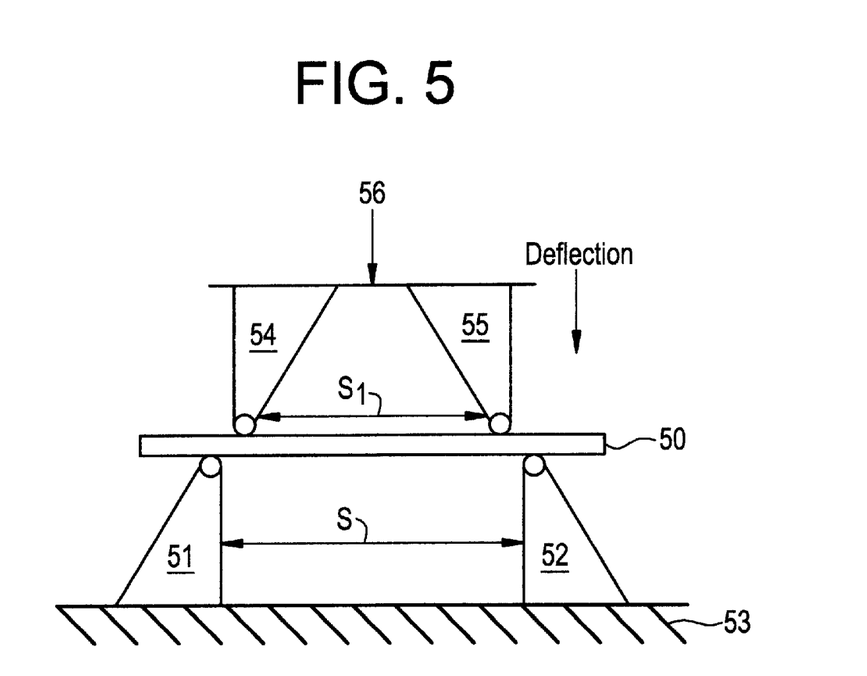
FIG. 5 is a schematical view of a four-point bend fixture and specimen arrangement used in bending tests performed on cylindrical specimens of explanted bone implants of this invention.

Referring to FIG. 5, four-point testing was performed on the specimens 50 of square, cross section, and rectangular shapes. Specimens 50 were placed on two supporting anvils 51 and 52 spaced apart a distance "s" of 50 mm on a solid base or floor 53. Load 56 was applied by via two upper anvils 54 and 55 with a spacing "$s_1$" of 50 mm at a displacement rate of 0.1 inches per minute until failure occurred (i.e., the specimen fractured). Values of flexural strength and modulus were recorded for each specimen.

While compression testing resulted in uniform stress states throughout the specimen, four-point bending induced more complex stresses based primarily on the ratio of the lower anvil spacing to upper anvil spacing and the thickness of the specimen. Bending theory states that the stresses in a beam in bending are zero in the center and maximum at the upper and lower surface. For this reason, the reported value of stress was replaced by a mathematically derived measure known as the flexural strength, which was an estimate of the stress at the surface of the specimen. This value was not the actual stress at the surface but is a commonly used means of comparison.

The definition of modulus for four-point bending and compression are the same but because of the different stress states, the values should not be directly compared.

Mechanical testing results:

Each of the response variables: 2% offset load; 2% offset stress; and modulus for the compression specimens, were summarized statistically and compared between treatment groups. The treatment code is given in Table 1.

TABLE 1

| Treatment Number | Treatment |
|---|---|
| 1 | Explanted specimens with 50 μm pore size |
| 2 | Explanted specimens with 95 μm pore size |
| 3 | Naive specimens with 50 μm pore size |
| 4 | Naive specimens with 90 μm pore size |

The summary statistics for compression testing are given in Table 2 below. The statistics are reported in terms of the mean value ± the standard deviation.

TABLE 2

| Treatment | N | 2% Offset Load (lbf) | 2% Offset Stress (psi) | Modulus (psi) |
|---|---|---|---|---|
| 1 | 5 | 37.4 ± 10.5 | 985.1 ± 298.6 | 11958.9 ± 5422.9 |
| 2 | 5 | 38.0 ± 4.3 | 1031.2 ± 102.7 | 11059.0 ± 3308.9 |
| 3 | 6 | 54.3 ± 3.9 | 1584.6 ± 119.3 | 32181.3 ± 6633.4 |
| 4 | 6 | 57.0 ± 3.5 | 1679.1 ± 135.7 | 36538.3 ± 7605.4 |

The offset load of the explanted specimens was approximately 35% lower than the naive specimens. This lower strength was consistent with wet condition exposure effects seen in MDC structures.

Each of the response variables, flexural stress and modulus for the bending specimens, were summarized statistically and compared between treatment groups. The treatment code is the same as that given above in Table 1. The bending specimen summary statistics are given in Table 3 below. The statistics are reported in terms of the mean value ± the standard deviation.

TABLE 3

| Variable | 50 μm microballoon specimen (mean ± std. dev.) | 95 μm microballoon specimen (mean ± std. dev.) |
|---|---|---|
| Load (lbf) | 23.8 ± 3.8 | 23.8 ± 2.2 |
| Energy (lbf-in) | 0.364 ± 0.08 | 0.377 ± 0.07 |
| Flexural Strength (psi) | 2311.0 ± 333 | 2313.0 ± 190 |
| Modulus (psi) | 175991 ± 14153 | 169041 ± 7374 |

ANOVA and paired t-test were performed to determine the significance of pore size and implantation on strength. A paired t-test was performed to compare the strength of explanted specimens from each of the two formulations. This t-test showed that the mean compressive strength, stress, and modulus were equivalent (p>0.759) between the two forms of explanted specimens.

An ANOVA was performed to simultaneously compare the mean compressive strength of naive and implanted specimens of both formulations. For each of the response variables at least one group's mean was significant (p<0.001). A Tukey's means comparison test was performed and showed that the unimplanted specimens were significantly stronger (p<0.002) than the implanted specimens.

A paired t-test was performed on the bending specimen data to determine to determine if the mean value of the mechanical test variables were significantly different between the two naive formulations of TPSF implant material. This comparison demonstrated that the strength of two naive formulations of TPSF implant material were equivalent (p>0.221). These data indicated that within the range of these two pore sizes the strength of the two TPSF implant material formulations were equivalent.

Histology methods:

Tissues for histology were placed in a buffered 10% formalin solution pH 7.0 (Statlab Medical Products, Dallas, Tex.). The implant was bisected longitudinally with the surrounding bone and embedded in methylmethacrylate (Fischer Scientific, Houston Tex.). Plastic sections were cut to 100 microns and reduced to approximately 20 microns by machine polishing using EXAKT cutting and grinding system. Hematoxyling and eosin stained sections were prepared and tissue evaluated for materials biocompatibility. Implanted materials were tested for the effect of materials formulation and pore size on bone ingrowth and biocompatibility.

Histology Results:

Histologic specimens showed a rectangular shaped implant residing deep in the tibia metaphysis. Since the implant was cylindrical and inserted transverse to the bone's long axis, the histologic section showed the sectioned implant as rectangular. This orientation permitted the TPSF implant material to contact cortical bone around the hole, medullarly tissue, the endosteum of the opposing cortex and the soft tissue overlying the drill site. This configuration permitted the evaluation of the TPSF implant material in relationship to several different tissue types.

All specimens showed intimate osseous adaption to significant portion of the implant's perimeter. In some cases, this adaption was direct and in others it was interposed with fibrocollagenous connective tissue which often contained osseous progenitor cells. Of special note was the observation of ingrowth of bone into the deep interstices of the material. Osteoid and mineralized bone was often seen generally distributed deep into the implant and far from the bone implant interface. Capillaries were seen deep in the implant supporting this type of bone formation.

Evaluation suggested that the more porous TPSF implant material formed within 95 mm silica microballoons and had more general and diffuse bone ingrowth. Quantitative histomorphometry was performed to determine the extent of bone infiltration and surface apposition to the implant, and the data results are summarized in Table 4. The quantitative histomorphometry mean and standard deviation statistics for these measurements are summarized in Table 5. The statistics are reported in terms of the mean value ± the standard deviation.

Implant area was constant and reflected the size of the implant. Total implant perimeter was the perimeter of the implant including that surface that was in direct apposition to the overlying soft tissue. Percent of new bone was the percent of the entire implant area measured that contained bone. This percent would be much higher if the TPSF implant material matrix was subtracted to give the total potential ingrowth area. Perimeter integrated with the new bone is the surface area of the implant covered with bone. Percent perimeter integrated is the total percent of the entire surface that was in direct contact with bone.

TABLE 4

| Animal (implant incl. 50 or 95 $\mu$m microballoons) | Total Implant Area Measured (mm$^2$) | New bone ingrowth (%) | Total Implant perimeter (mm) | Perimeter Integrated with New Bone(mm) | Perimeter Integrated (%) |
|---|---|---|---|---|---|
| 1A (50 $\mu$m) | 8.97 | 1.8 | 19.5 | 17.2 | 88 |
| 1A (95 $\mu$m) | 8.97 | 5 | 22.3 | 9.4 | 42 |
| 2A (50 $\mu$m) | 8.97 | 2.7 | 22.5 | 14.7 | 65.3 |
| 2A (95 $\mu$m) | 8.97 | 2 | 22.6 | 19.8 | 87.6 |
| 3A (50 $\mu$m) | 8.97 | 0.5 | 23.9 | 14.2 | 59.4 |
| 3A (95 $\mu$m) | 8.97 | 2.7 | 19.9 | 16.8 | 84.4 |
| 4A (50 $\mu$m) | 8.97 | 5.2 | 21.7 | 14.7 | 67.7 |
| 4A (95 $\mu$m) | 8.97 | 0.5 | 23.4 | 19.9 | 85 |
| 5A (50 $\mu$m) | 8.97 | 0.1 | 17.8 | 9.6 | 53.9 |
| 5A (95 $\mu$m) | 8.97 | 3.34 | 23.5 | 19.5 | 83 |

TABLE 5

| TPSF Implant Material Formulation | New bone ingrowth (%) | Total Implant perimeter (mm) | Perimeter Integrated with New Bone (mm) | Perimeter Integrated (%) |
|---|---|---|---|---|
| 50 $\mu$m microballoons | 2.8 ± 1.6 | 22.3 ± 1.5 | 16.1 ± 4.3 | 71.9 ± 18.6 |
| 95 $\mu$m microballoons | 1.9 ± 1.9 | 21.1 ± 2.4 | 15.1 ± 3.8 | 71.3 ± 15.8 |

A t-test was performed to test the equivalence of the mean bone ingrowth and surface apposition response to TPSF implant material. The test determined that there was no significant difference (p>0.445) in the extent of bone ingrowth or apposition between the two forms of TPSF implant material tested (i.e., 50 and 95 mm microballoon containing). This analysis was remarkable in the extent of bone ingrowth or apposition between the two forms of the implant that was originally contacting soft tissue was eliminated from the perimeter measurement, the bone surface apposition measurement would result in over 90% of the implant surface coated in bone. This approach was not used because some of the implants had bone forming between the implant and soft tissue and this total perimeter measurement was used to interpret this effect.

Histologic evaluation showed that the rabbit tibial metaphysis was generally void of cancellous bone. This characteristic of the rabbit was surmised as possibly impacting the extent of bone infiltration into the implant. In spite of the site not having any appreciable cancellous bone at the time of implantation, bone formed around the vast majority of the implant that was deep within the medullarly space.

The foregoing summarized test results showed that the two tested TPSF implant material formulations were equivalent in strength in the naive and explanted form. Strength of the TPSF implant material specimens was found to be greater than human cancellous bone taken from the tibia of a 35 year old deceased human male. TPSF implant material's 2% offset yield stress for the explanted specimen was 985 psi and for the unimplanted was 1679 psi. Compression testing of human cancellous bone, measured fresh frozen then thawed, failed at a stress of 366 psi, and following hydrochloric acid (HCl) treatment, its mean strength decreased to 240.9 psi. HCl treatment is used in the allograft bone industry to demineralize bone for human implant use. TPSF implant material has a 358% strength advantage over fresh human bone and a 169% compressive strength advantage when wet and partially infiltrated with mineralized bone and osteoid. Though strong in compression, this material can be cut with a scalpel to match anatomical requirements.

The histologic evaluations showed that both formulations were highly biocompatible, formed a bone-implant interface that was often not interposed with fibrous tissue, and formed bone deep into the implant.

Example 2

Biocompatibility and osteoconduction in a bone healing rabbit model were conducted using New Zealand White rabbits to evaluate in vivo the use of thermoplastic syntactic foam (TPSF implant material) and, as a comparison material, an alumina-enhanced thermal barrier (AETB) space shuttle ceramic foam (density=about 16 lb/ft$^3$) was used as synthetic bone.

Experimental methods:

Compositions were placed in bone defects created above the ear on both sides of the skull of each subject. More specifically, to demonstrate the maxillofacial applications, small rectangular pieces (approximately 5×4×2 mm) were implanted subperiosteally in a shallow skull defect. The bone defect was created with a burr on each side of the calvarium mid sagittal suture. The defect did not penetrate the skull.

Periosteum and skin were closed over the implant. Following a 12 week healing period for osseous integration, the implants were retrieved from the animal subjects and evaluated for biocompatibility and bone ingrowth.

Tissues used for histological and histomorphometric analysis were fixed in 10% neutral buffered formalin. The samples were dehydrated through a graded series of alcohol, xylene, and infiltrated with Technovit Resin, obtained from Technologies, Inc. Specimens were then embedded for sectioning in a longitudinal plane and sectioned at 10 $\mu$m. Serial sections were stained with hematoxylin and eosin for histologic analysis. Representative slides were selected and examined via SEM at 16× original magnification and up to 250× magnification as needed to evaluate the histologic response to the material.

Results:

There was no evidence of adverse host response to the test specimens from either the ceramic foam or TPSF implant material formulations, except for one ceramic foam specimen which had a mild inflammatory response. Specifically, there was no foreign body giant cell reaction macrophage infiltrate abscess or acute and chronic inflammatory response to any of the other materials.

Due to the nature of the animal model, many of the implants had been displaced from bone and were in the overlying soft tissue. This displacement was anticipated due the shallow defect and the ability and common nature of the rabbit to scratch its head. This mechanical action caused motion of the implant and in many cases and with most materials, encapsulation of the implant with fibrous connective tissue. Therefore, the results were otherwise ignored for the subjects found to have such displaced implants.

Of those subjects having implants that remained in position is situ in bone or adjacent to bone structure, osseous apposition to the surface of the material was common. In the case of TPSF implant material, bone nucleation often occurred within the material when at least one surface of TPSF implant material was adjacent to bone.

The overlying soft-tissue was observed to be normal for both the ceramic foam or TPSF implant material implants.

Both the ceramic foam and TPSF implant materials were in direct apposition with the underlying bone of the skull. SEM examination revealed that none of the ceramic foam implants showed any evidence of bone filtration, although reactive new bone was forming at the interface of ceramic foam implants. That is, stained bone was observed by SEM to be in direct contact with reactive bone in focal areas. In general, an interpositioned fibrous tissue layer had formed between the ceramic foam materials and bone. Scant bone ingrowth was apparent in this section.

In contrast, the TPSF implant material showed direct apposition of bone to the margins of the material as well as nucleation of bone within the matrix of the TPSF implant material. As was observed by SEM, stained bone had focal communication with the surface of the implant. No fibrous tissue was seen formed between the implant and bone. The stained periosteum was seen to be formed over the implant, and no adverse response was apparent. As even better seen at 40× magnification via SEM, bone nucleation into the inventive TPSF implant materials was seen forming between the microballoons to form a living composite containing TPSF implant material components. Semi-spherical elements of the bulk TPSF implant material implant were observed as having had migrated into the medullary compartment and were is surrounded by a delicate fibro-fatty marrow further indicative of the biocompatibility of TPSF implant material. This nucleation of bone within the material appeared unique in that it was forming at sites within the material that were distant from the materials interface with bone. Small spherical fragments of the material were incorporated into adjacent bone and sitting in medullary tissue. These fragments did not cause any adverse response.

The phenomena of TPSF implant material having natural bone formed interstitially within its matrix at sites distant and otherwise remote from the actual interface of the TPSF implant material with natural bone in the host was remarkable and surprising. While not desiring to be bound to any particular theory at this time, it nonetheless is thought that the ingrowth phenomena may be attributable to the interaction of natural bone, with its intrinsic piezoelectric properties, and the dielectric properties of TPSF implant material. More specifically, the medical literature has reported that electrical current within bone or soft tissue tends to change with an injury. Therefore, the ingrowth phenomena observed for the TPSF implant material implants of the present invention may be attributable to these electric fields assisting in recruitment of osteoprogenitor cells to the site to differentiate and mature into osteoblast with the potential to form bone within a defect or an TPSF implant material. By the introduction of conductive carbon fibers into the foam, the dielectric properties of the TPSF can be altered for optimization of intrinsic bone growth.

In any event, while both the ceramic foam and inventive TPSF implant material were observed to be highly biocompatible in soft and hard tissue, the ceramic foam comparison structure was too dense to permit bone to infiltrate within the materials.

Although presently preferred embodiments of the present invention have been described in detail hereinabove, it should be clearly understood that many variations and/or modifications of the basic inventive concepts herein taught, which may appear to those skilled in the pertinent art, will still fall within the spirit and scope of the present invention, as defined in the appended claims.

What is claimed is:

1. An implant material for replacing or augmenting living bone tissue, comprising:

about 85 to 3 parts by volume microballoons per 100 parts by volume of the implant material;

about 3 to 85 parts by volume polymer per 100 parts by volume of the implant material, wherein the polymer is wetted to the microballoons and binds the microballoons together in an array; and about 3 to 70 parts by volume interstitial space between the microballoons in the array per 100 parts by volume of the implant material.

2. The implant material as claimed in claim 1, wherein the microballons comprise from about 25 to 70 parts by volume per 100 parts by volume of the implant material, and the polymer comprises from about 15 to 30 parts by volume per 100 parts by volume of the implant material.

3. The implant material as claimed in claim 1, wherein the interstitial space between the microballoons contains air.

4. The implant material as claimed in claim 1, wherein the microballons comprise silica microballoons.

5. The implant material as claimed in claim 1, wherein the microballoons comprise at least 90% thereof silica microballoons having a diameter ranging from about 5 µm to about 150 µm.

6. The implant material as claimed in claim 1, further including a fiber material embedded within the array.

7. The implant material as claimed in claim 1, wherein the polymer comprises a polycondensate polymer.

8. An implant material for replacing or augmenting living bone tissue, comprising:

microballoons;

polyetherimide polymer, wherein the polyetherimide polymer is wetted to the microballoons and binds the microballoons together in an array; and interstitial space between the microballoons in the arrays, wherein the interstitial space between the microballoons comprises from about 3 to 70 parts by volume per 100 parts by volume of the implant material.

9. The implant material as claimed in claim 8, wherein the polyetherimide polymer is the polymerization product of an oligomeric precursor.

10. The implant material as claimed in claim 8, wherein the polyetherimide polymer is the polymerization product of an oligomeric precursor having an initial viscosity at the processing temperature of from about 330° C. to about 350° C. sufficient to flow and to set said microballoons prior to polymerization.

11. The implant material as claimed in claim 8, wherein the microballoons comprise silica microballoons.

12. The implant material as claimed in claim 8, wherein the microballoons comprise at least 90% thereof silica microballoons having a diameter ranging from about 5 µm to about 150 µm.

13. The implant material as claimed in claim 8, wherein the microballoons comprise from about 85 to 3 parts by volume per 100 parts by volume of the implant material, the polyetherimide polymer comprises from about 3 to 85 parts by volume per 100 parts by volume of the implant material, and the interstitial space between the microballoons comprises from about 3 to 70 parts by volume per 100 parts by volume of the implant material.

14. The implant material as claimed in claim 8, wherein the interstitial space between the microballoons contains air.

15. The implant material as claimed in claim 8, further including a fiber material embedded within the array.

16. An implant material for replacing or augmenting living bone tissue, comprising:

microballoons;

a polymer which is wetted to the microballoons and binds the microballoons together in an array;

interstitial space between the microballoons in the array; and a fiber material embedded within the array, wherein the fiber material comprises from about 0.1 to 20 parts by volume per 100 parts by volume of the implant material.

17. The implant material as claimed in claim 16, wherein said first component comprises silica microballoons and the polymer comprises polyetherimide polymer.

* * * * *